(12) United States Patent
Apelqvist et al.

(10) Patent No.: US 11,418,866 B2
(45) Date of Patent: Aug. 16, 2022

(54) VOICE-ACTIVATED SOUND ENCODING FOR HEADSETS USING FREQUENCY DOMAIN REPRESENTATIONS OF MICROPHONE SIGNALS

(71) Applicant: 3M INNOVATIVE PROPERTIES COMPANY, St. Paul, MN (US)

(72) Inventors: Stefan M. Apelqvist, Värnamo (SE); Vijay K. Gidla, Värnamo (SE); Abel Gladstone Mangam, Värnamo (SE); Roger Kihlberg, Värnamo (SE)

(73) Assignee: 3M Innovative Properties Company, St. Paul, MN (US)

( * ) Notice: Subject to any disclaimer, the term of this patent is extended or adjusted under 35 U.S.C. 154(b) by 70 days.

(21) Appl. No.: 15/733,658

(22) PCT Filed: Mar. 26, 2019

(86) PCT No.: PCT/IB2019/052460
§ 371 (c)(1),
(2) Date: Sep. 25, 2020

(87) PCT Pub. No.: WO2019/186403
PCT Pub. Date: Oct. 3, 2019

(65) Prior Publication Data
US 2021/0014599 A1    Jan. 14, 2021

Related U.S. Application Data

(60) Provisional application No. 62/649,852, filed on Mar. 29, 2018.

(51) Int. Cl.
*G06F 3/16*     (2006.01)
*H04R 1/10*    (2006.01)
(Continued)

(52) U.S. Cl.
CPC ............ *H04R 1/1041* (2013.01); *G10L 15/22* (2013.01); *G10L 19/00* (2013.01); *G10L 21/02* (2013.01); *G10L 25/78* (2013.01); *H04R 2410/05* (2013.01)

(58) Field of Classification Search
CPC ... H04R 1/1041; H04R 2410/05; G10L 15/22; G10L 25/78; G10L 21/02; G10L 19/00; H04M 9/082
(Continued)

(56) References Cited

U.S. PATENT DOCUMENTS 5,251,263  A       10/1993  Andrea
6,002,950  A  *   12/1999  Muraoka ............... H04M 9/082
                                                                    455/550.1
(Continued)

FOREIGN PATENT DOCUMENTS

EP              2555189         2/2013
WO    WO 2016-039904    3/2016
WO    WO 2017-205107    11/2017

OTHER PUBLICATIONS

International Search Report for PCT International Application No. PCT/IB2019/052460, dated Jun. 13, 2019, 6 pages.

*Primary Examiner* — Md S Elahee
(74) *Attorney, Agent, or Firm* — Katherine M. Scholz

(57) ABSTRACT

A voice-activated encoding method includes determining a voice power parameter based on a frequency domain representation of a voice signal from a voice microphone. The method includes determining an ambient power parameter based on a frequency domain representation of at least one ambient signal from at least one ambient microphone spaced from the voice microphone. The method also includes enabling encoding of an audio signal based on the voice signal in response to comparing the power parameters and a threshold value. A headset including a controller may use the (Continued)

method to determine whether to enable or disable encoding, transmission, or both of an audio signal to another device.

20 Claims, 10 Drawing Sheets

(51) Int. Cl.
    *G10L 15/22*     (2006.01)
    *G10L 19/00*     (2013.01)
    *G10L 21/02*     (2013.01)
    *G10L 25/78*     (2013.01)

(58) Field of Classification Search
    USPC .......................................................... 704/275
    See application file for complete search history.

(56) References Cited

U.S. PATENT DOCUMENTS

| | | |
|---|---|---|
| 6,526,148 B1 | 2/2003 | Jourjine |
| 2002/0080987 A1 | 6/2002 | Almqvist |
| 2004/0042626 A1 | 3/2004 | Balan |
| 2005/0070337 A1 | 3/2005 | Byford |
| 2007/0021958 A1 | 1/2007 | Visser |
| 2008/0260180 A1 | 10/2008 | Goldstein |
| 2009/0010456 A1 | 1/2009 | Goldstein |
| 2009/0089053 A1 | 4/2009 | Wang |
| 2011/0288860 A1 | 11/2011 | Scheveiw |
| 2016/0118062 A1 | 4/2016 | Usher |

\* cited by examiner

VOICE-ACTIVATED SOUND ENCODING FOR HEADSETS USING FREQUENCY DOMAIN REPRESENTATIONS OF MICROPHONE SIGNALS

CROSS REFERENCE TO RELATED APPLICATIONS

This application is a national stage filing under 35 U.S.C. 371 of PCT/IB2019/052460, filed Mar. 26, 2019, which claims the benefit of U.S. Provisional Application No. 62/649,852, filed Mar. 29, 2018, the disclosure of which is incorporated by reference in its/their entirety herein.

BACKGROUND

Noisy environments, such as worksites, airfields, helipads, and the like, may include noise sources that have the potential to damage the hearing of a person. A person operating in a noisy environment may experience hearing loss from acute acoustic trauma or gradually developing noise-induced hearing loss. To help prevent hearing damage, a person operating in a noisy environment may wear hearing protection. Hearing protection may be passive or active. Passive hearing protection may use earplugs and earmuffs that block noise up to a particular noise level. Active hearing protection may use earmuffs that permit certain types of noise to pass through to a person by electronically filtering out particular decibels or frequencies.

Although various forms of hearing protection may provide adequate protection against excessive noise, persons wearing such hearing protection may need to communicate with one another. In noisy environments, communicating with one another may be difficult while wearing hearing protection due to noise from noise sources and filtering from the hearing protection. In some scenarios, a person wearing hearing protection may carry an additional and separate communication device to facilitate communication with other individuals in a noisy environment. Although separate communication devices may facilitate such communication, the person may be required to carry two separate devices (e.g., hearing protection and communication device).

Voice Operated eXchange (VOX) has been used to facilitate voice communication between headsets. In general, VOX transmits sound to another headset when voice activity is detected. However, traditional voice activity detection in existing VOX-enabled headsets may not perform well in high-noise environments or non-stationary noise environments. In particular, traditional voice activity detection algorithms have difficulty distinguishing speech from noise in a loud ambient environment and continually encode and transmit sound even when there is no speech. This may lead to reduced battery life between charges and poor clarity in communications with other people, which means traditional voice activity detection may be unsuitable for use with hearing protection headsets in some environments.

SUMMARY

Various aspects of the present application relate to voice-activated sound encoding for headsets using frequency domain representations of microphone signals, which may be particularly suitable for hearing protection applications. Voice-activated sound encoding may use signals from at least two microphones, such as a voice microphone and an ambient microphone. The microphone signals may be transformed into frequency domain representations and the power of the signals compared in one or more selected frequency bands. Voice activation may be determined based on the comparison. Selecting frequency bands that correspond to speech and using a relative comparison between signals may provide robust voice activity detection, or VOX functionality, in high noise environments or non-stationary noise environments. Employing this voice-activated sound encoding technique may lead to improved power savings and more desirable performance of a communications headset in hearing protection applications.

In one aspect, a device may include a voice microphone configured to generate a voice signal based on sound detected at the voice microphone. The device may also include at least one ambient microphone spaced from the voice microphone and configured to generate at least one ambient signal based on sound detected at the at least one ambient microphone. The device may further include a controller operably coupled to the microphones. The controller may include a communications encoder configured to encode an audio signal for transmission to another device. The controller may be configured to determine a voice power parameter based on a frequency domain representation of the voice signal. The controller may also be configured to determine an ambient power parameter based on a frequency domain representation of the at least one ambient signal. The controller may further be configured to, in response to a determination that is based at least in part on the power parameters and a threshold value, encode, using the communications encoder, an audio signal based on the voice signal.

In another aspect, a controller may include an input interface configured to receive a voice signal and at least one ambient signal. The controller may also include an output interface configured to provide an audio signal based on the voice signal. The controller may further include a memory configured to store a representation of the voice signal and the ambient signal. In addition, the controller may include a processor operably coupled to the input interface, the output interface, and the memory. The processor may be configured to determine a voice power parameter based on a frequency domain representation of the voice signal. The processor may also be configured to determine an ambient power parameter based on a frequency domain representation of the at least one ambient signal. The processor may further be configured to, in response to a determination that is based at least in part on the power parameters and a threshold value, encode an audio signal based on the voice signal.

In another aspect, a method may include determining a voice power parameter based on a frequency domain representation of a voice signal from a voice microphone. The method may also include determining an ambient power parameter based on a frequency domain representation of at least one ambient signal from at least one ambient microphone spaced from the voice microphone. The method may further include encoding, using a microprocessor, an audio signal based on the voice signal in response to a determination that is based at least in part on the power parameters and a threshold value.

BRIEF DESCRIPTION OF THE DRAWINGS

The drawings of this application may be briefly described as follows.

DETAILED DESCRIPTION

Figure 1:
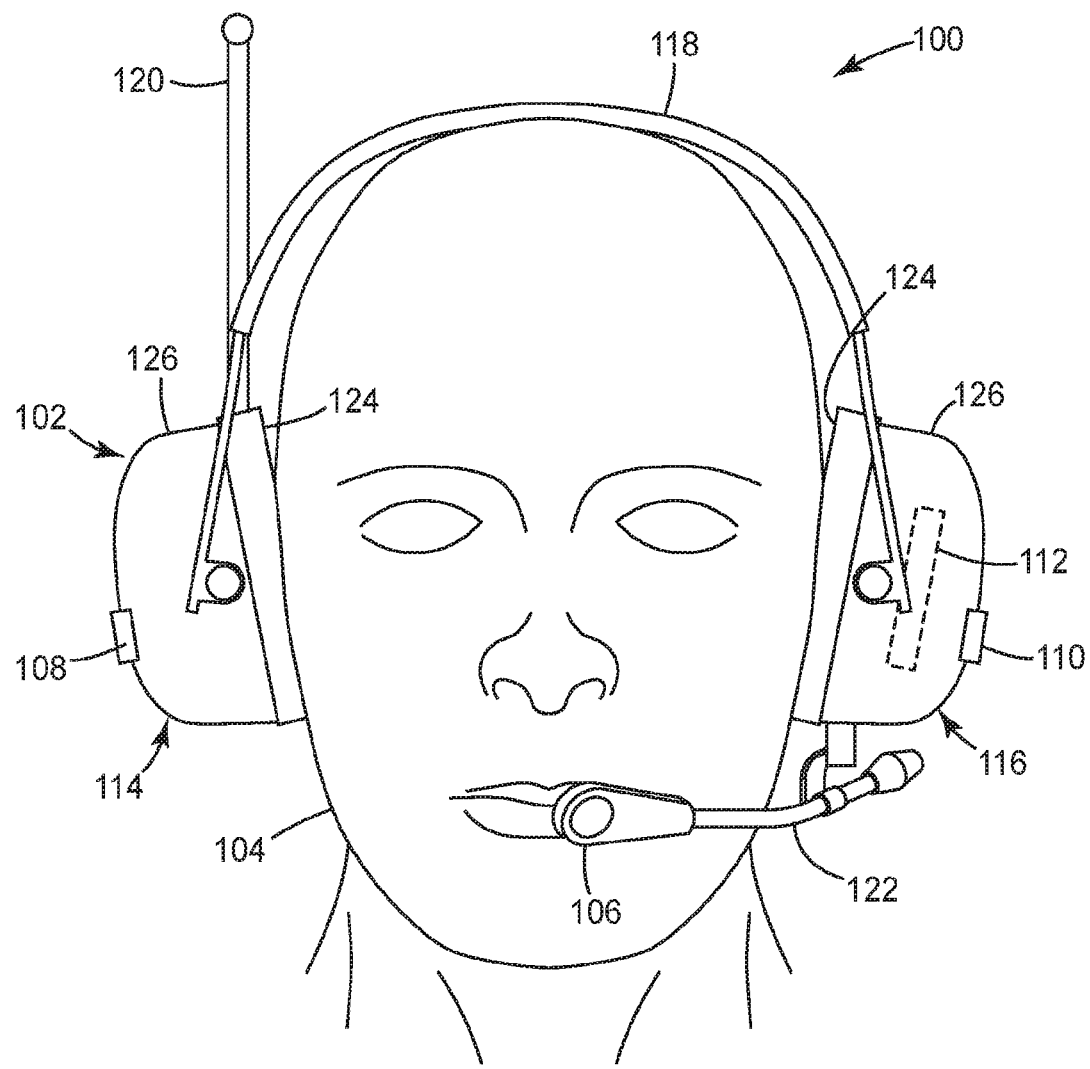
FIG. 1 is an illustration of a headset according to one embodiment of the present application.

The present application relates to headsets. In particular, the present application relates to voice-activated sound encoding for headsets using frequency domain representations of microphone signals for improved power savings and performance in noisy environments. Although reference is made to headsets, such as communication headsets for hearing protection, the voice-activated sound encoding technique described herein may be used with any device that receives two different types of noise from different microphones, such as a mobile radio unit with internal and external microphones. Various other applications will become apparent to one of skill in the art having the benefit of the disclosure of the present application.

By eliminating the need to carry additional communications equipment, the weight of communications equipment carried by the user may be reduced thereby improve the range of motion and/or movement of the user. Providing accurate detection of a user's voice in a noisy environment may improve communication with other people. Further, accurate voice detection may facilitate improved conservation of battery power and longer times between charging (e.g., less recharging and/or down time) by disabling certain functions when the user is not talking. Still further, providing accurate voice detection despite a limited space between microphones may facilitate performance suitable for headsets used in hearing protection applications.

The present application provides voice-activated sound encoding that may be used in various methods, systems, and apparatuses related to communication between headsets. In voice communications headsets, a voice-activated sound encoding method may include determining a voice power parameter based on a frequency domain representation of a voice signal from a voice microphone; determining an ambient power parameter based on a frequency domain representation of at least one ambient signal from at least one ambient microphone spaced from the voice microphone; and encoding of an audio signal based on the voice signal in response to a determination that is based at least in part on the power parameters and a threshold value. Encoding may be disabled in response to comparing the power parameters and a disable threshold value, which may be the same or different than the threshold value. The one or both thresholds may be determined, for example, using trial and error. In particular, the comparison between power parameters in one or more selected frequency bands may include determining a ratio between the power parameters. Relative comparison of power parameters in one or more selected frequency bands may allow for robust detection of voice activity using a simple threshold. For example, the ratio may be compared to the threshold value. The frequency domain representations of microphone signals may also be used to provide an enhanced audio signal, which may be encoded and transmitted by the headset. The frequency domain representations may be used as inputs into a noise reduction algorithm to produce the enhanced audio signal.

The drawings of this application, which depict one or more aspects of the disclosure of the present application, are described herein in more detail. It will be understood that other aspects not depicted in the drawings or explicitly described herein may be considered within the scope of this disclosure, for example, when considered by a person having ordinary skill in the art.

FIG. 1 illustrates an environment 100 for using communications headset 102, which may be worn by a person or user 104 for hearing protection. Headset 102 includes one or more microphones. Each microphone 106, 108, 110 may be described as a device that translates sound into a signal (e.g., an electrical signal) representing detected sound. For instance, user 104 wearing headset 102 may speak, thereby generating sound that is received by one of the microphones. Signals from one or more of microphones 106, 108, 110 may be used to determine whether the user's voice is detected.

As shown, headset 102 includes voice microphone 106 (e.g., boom microphone), first ambient microphone 108 (e.g., proximate to the right ear), and second ambient microphone 110 (e.g., proximate to the left ear). Voice microphone 106 may be described as providing a voice signal, and each ambient microphone 108, 110 may be described as providing an ambient signal. Each microphone 106, 108, 110 may be spaced from at least one of the other microphones in any direction. Each microphone 106, 108, 110 may have a directivity and proximity effect, which may be used to filter out low frequencies at one or more distances (e.g., beyond a certain distance). For example, voice microphone 106 may have a polar pattern that is hypercardioid, which may give a maximum response at 0 degrees of orientation (e.g., directed at the mouth of user 104). The frequency response of voice microphone 106 may be different than ambient microphones 108, 110. Ambient microphones 108, 110 may have a different directivity than voice microphone 106, for example, omnidirectional. The frequency response of ambient microphones 108, 110 may have substantially the same magnitude in all or substantially all directions and/or frequencies.

As shown, headset 102 includes first earpiece 114 and second earpiece 116. Earpieces 114, 116 may be coupled by headband 118 (e.g., a stirrup) extending between the earpieces. Headband 118 may be formed of any rigid or semi-rigid material, such as plastic, aluminum, steel, or any other suitable material. Headband 118 may be used to secure headset 102 to the user's head. In some embodiments, headband 118 may be used to space first and second ambient microphones 108, 110 from one another.

Each earpiece 114, 116 may include, or be coupled to, one of the ambient microphones 108, 110. In the illustrated embodiment, first earpiece 114 includes first ambient microphone 108 and second earpiece 116 includes second ambient microphone 110.

Each of microphone 106, 108, 110 may be operably coupled to controller 112 by wireless or wired connection, for example, using interconnect. Examples of interconnect allowing wired communication between various components of headset 102 include one or more strands of wire formed of copper, aluminum, silver, or other suitable conductive material. Some interconnect may be coupled to headband 118, for example, to provide a connection between earpiece 114 and earpiece 116.

Controller 112 may be used to determine whether the user's voice is detected based on signals from one or more microphones 106, 108, 110. As illustrated, controller 112 is located in second earpiece 116. In general, some or all of controller 112 may be coupled to first earpiece 114, second earpiece 116, headband 118, or any combination thereof.

Headset 102 may include one or more antennas, such as antenna 120, to transmit and/or receive signals from other devices remote to the headset. As illustrated, antenna 120 extends from earpiece 114. Antenna 120 may be operably coupled to controller 112 by wireless or wired connection, for example, using interconnect. In general, some or all of antenna 120 may be coupled to first earpiece 114, second earpiece 116, headband 118, or any combination thereof.

Microphone 106 may be coupled to boom 122, which may position voice microphone 106 proximate to the user's mouth. As illustrated, boom 122 extends from second earpiece 116. In general, boom 122 may be coupled to first earpiece 114, second earpiece 116, headband 118, or any combination thereof. In some embodiments, boom 122 may be used to space voice microphone 106 from one or both ambient microphones 108, 110.

Earpieces 114, 116 may be designed to provide at least some passive or active hearing protection for user 104. Each earpiece 114, 116 may include cushion 124 coupled to cup portion 126 of the earpiece. In particular, each cushion 124 and cup portion 126 may form an acoustic barrier around each ear of user 104. Cushions 124 may abut around the ears of user 104. Cushions 124 may contribute to the capability of earpieces 114, 116 to dampen or otherwise reduce ambient sound from an environment outside of the earpieces. Cushions 124 may be formed of any compressible and/or expanding material, such as foam, gel, air, or any other such suitable material. Cup portions 126 may be formed of any rigid or semi-rigid material, such as a plastic, which in some cases, may be a non-conductive, dielectric plastic.

Each cup portion 126 may include a speaker (not shown), such as a loudspeaker, to emit sound corresponding to a signal (e.g., an electrical signal). In particular, each speaker cup portion 126 may be positioned to direct sound into the interior of the cup formed by the cup portion. When headset 102 is in use, the interior of each cup portion 126 may be positioned adjacent to an ear of user 104. Each speaker may emit sound based on a signal received or generated by other components of headset 102, such as controller 112. In particular, each speaker may be operably coupled to controller 112 by wireless or wired connection, for example, using interconnect that may be coupled to headband 118. Each speaker may include one or more electroacoustic transducers that convert electrical audio signals into sound. Some speakers may include one or more of a magnet, a voice coil, a suspension and diaphragm structure, or a membrane.

One or more of the components, such as controllers, microphones, or speakers, as described herein may include a processor, such as a central processing unit (CPU), computer, logic array, or other device capable of directing data coming into or out of headset 102. The controller may include one or more computing devices having memory, processing, and communication hardware. The controller may include circuitry used to couple various components of the controller together or with other components operably coupled to the controller. The functions of the controller may be performed by hardware and/or as computer instructions on a non-transient computer readable storage medium.

The processor of the controller may include any one or more of a microprocessor, a microcontroller, a digital signal processor (DSP), an application specific integrated circuit (ASIC), a field-programmable gate array (FPGA), and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller could utilize other components such as relays and timers to achieve the desired results, either alone or in combination with a microprocessor-based system.

In one or more embodiments, the exemplary systems, methods, and interfaces may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other devices and/or methods as described herein or as would be applied in a known fashion. In view of the above, it will be readily apparent that the controller functionality as described herein may be implemented in any manner known to one skilled in the art.

With various components of headset 102 being described, the voice-activated encoding functionality of the headset will be described in more detail herein with reference to FIG. 2.

Figure 2:
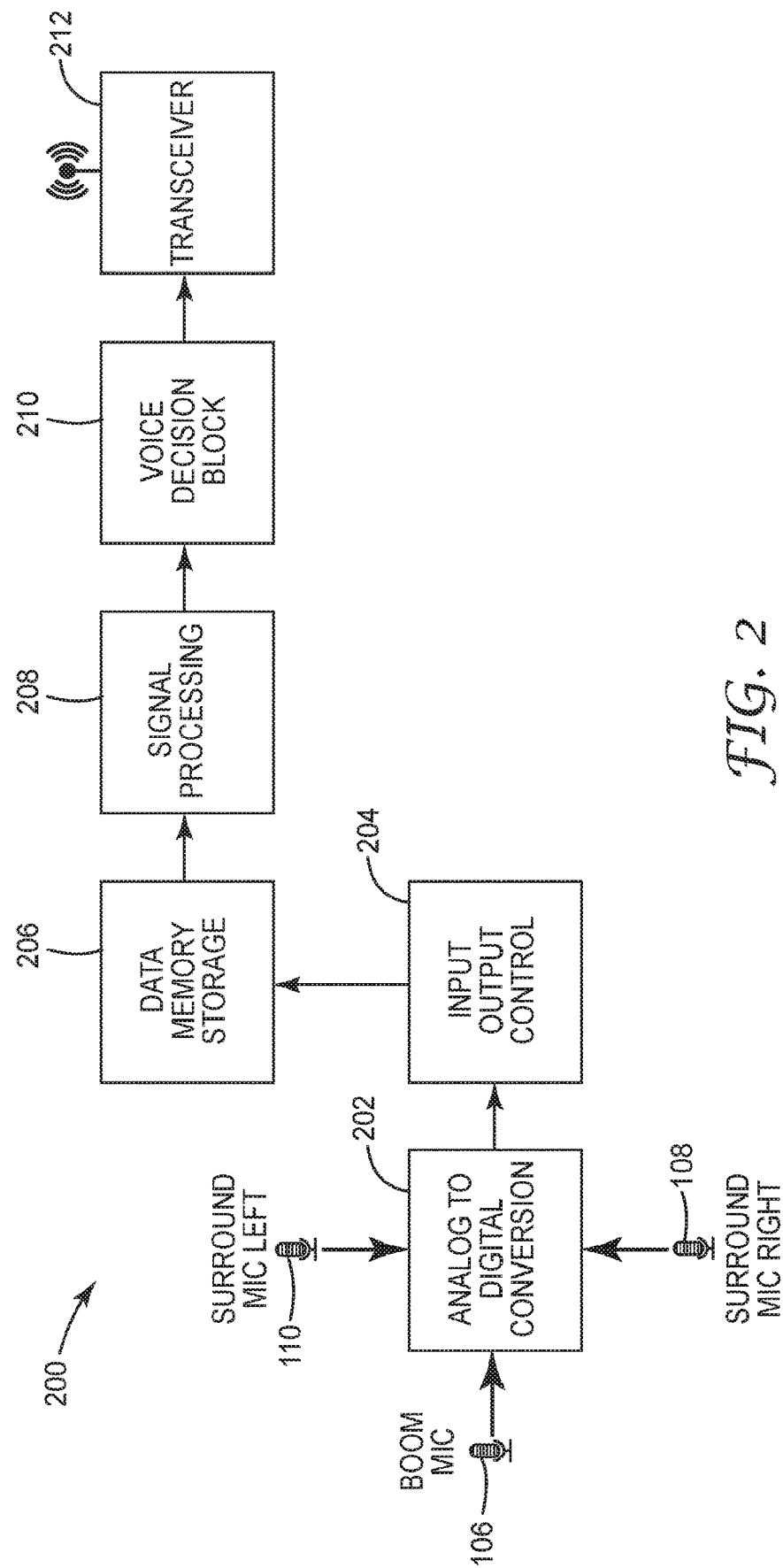
FIG. 2 is a flow diagram of one method of voice-activated encoding for use with the headset of FIG. 1 according to one embodiment of the present application.

FIG. 2 illustrates a flow diagram example of high-level architecture method 200 of voice-activated encoding for headset 102 (FIG. 1). One or more parts of method 200 may be performed by components of controller 112 (FIG. 1). Method 200 may include analog-to-digital conversion 202 of microphone signals, for example, from voice microphone 106 and from at least one of first ambient microphone 108 and second ambient microphone 110. In general, the microphones 106, 108, 110 provide analog signals representing sound for signal processing. Analog-to-digital conversion 202 produces a digital representation of each microphone signal. Analog-to-digital conversion 202 may be performed by any suitable processor, such as an analog-to-digital converter (ADC). Each microphone 106, 108, 110 may be operably coupled to a different ADC or different inputs of one or more ADCs to perform analog-to-digital conversion 202.

The microphone signals may be received for input-output control 204. Then, the microphone signals may be provided, or routed, to data memory storage 206. The microphone signals may be retrieved from memory (e.g., by a processor, such as a central processing unit, or CPU) for signal processing 208.

Signal processing 208 may provide a frequency domain representation of each microphone signal. The frequency domain representation provides information, such as magnitude and/or phase information, about the signal for one or more frequencies or frequency bands.

Signal processing 208 may perform digital signal processing and/or analog signal processing (e.g., on analog microphone signals without analog-to-digital conversion 202) to provide a frequency domain representation of the microphone signals. For example, an analog filter bank may be used.

Each microphone signal may represent sound energy. Signal processing 208 may provide a power parameter for each microphone signal based on the sound energy. In particular, each power parameter may be determined based on the frequency domain representation of the respective microphone signal in one or more selected frequency bands. The selected frequency bands may correspond to frequencies common to speech. Comparing power parameters in one or more selected frequency bands corresponding to speech may provide robust isolation of speech frequencies from various ambient noise frequencies that advantageously uses the positioning of a voice microphone proximate the user's mouth and an ambient microphone positioned farther away.

Using information provided by signal processing 208, voice decision block 210 may determine whether to enable or disable voice encoding and/or transmission from headset 102. When voice decision block 210 enables voice encoding and/or transmission, an audio signal based on the analog or digital microphone signal may be provided to transceiver 212 for transmission, for example, to another headset or other communications device.

In general, encoding and transmitting audio signals based on microphone signals use more processing resources and/or battery power than various signal processing 208 described herein. Using signal processing 208 and voice decision block 210 may save processing resources and/or battery power during operation of headset 102 to facilitate increased time between charges.

Figure 3:
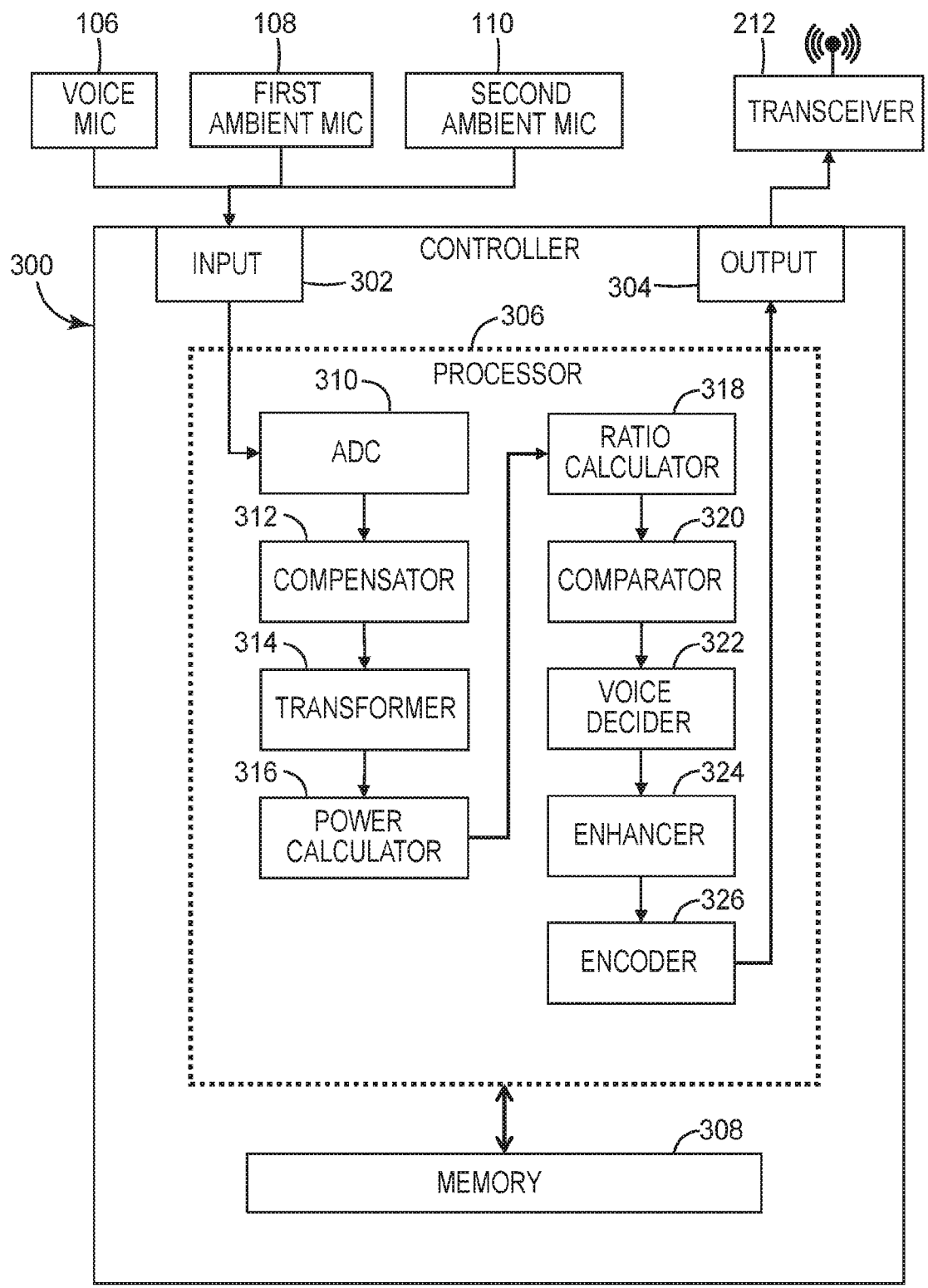
FIG. 3 is a schematic illustration of a controller for use with the headset of FIG. 1 according to one embodiment of the present application.

FIG. 3 illustrates schematically an example of controller 300 for headset 102 (FIG. 1) configured for voice-activated encoding. As illustrated, controller 300 includes input interface 302, which may be operably coupled to one or more of voice microphone 106, first ambient microphone 108, and second ambient microphone 110 and may be configured to receive one or more microphone signals. Controller 300 includes output interface 304, which may be operably coupled to transceiver 212 and may be configured to provide an audio signal to the transceiver. Transceiver 212 may include various components wirelessly transmit and/or receive communications, such as an audio signal to or from another device and may be coupled to, or include, antenna 120 (FIG. 1). In some embodiments, transceiver 212 may be considered part of controller 300.

Input interface 302 and output interface 304 may be operably coupled to processor 306 and/or memory 308. Processor 306 may execute one or more modules. Modules may include hardware (e.g., an integrated circuit chip) and/or software (e.g., instructions stored in memory 308). Modules of processor 306 may include analog-to-digital converter (ADC) 310, compensator 312, transformer 314, power calculator 316, ratio calculator 318, comparator 320, voice decider 322, enhancer 324, or encoder 326.

Processor 306 may include ADC 310. As illustrated, ADC 310 may receive one or more analog signals representing sounds detected by microphones 106, 108, 110 and convert each analog signal into digital form (e.g., using hexadecimal digits). Any suitable resolution may be used, for example, a 32-bit signed integer level of resolution.

The resulting digital signals from ADC 310 may be provided to compensator 312. Each microphone 106, 108, 110 may have a different frequency response, particularly between voice microphone 106 and ambient microphones 108, 110. Compensator 312 may correct one or more of the digital signals based on differences between various frequency responses of microphones 106, 108, 110. In some embodiments, compensator 312 corrects the digital signal from one or both ambient microphones 108, 110 based on frequency response differences compared to voice microphone 106.

Transformer 314 may receive one or more compensated digital signals and provide a frequency domain representation of each compensated digital signal. Any suitable technique for determining and providing a frequency domain representation may be used, such as a Discrete Fourier Transform (e.g., a Fast Fourier Transform), a filter bank, or a wavelet transform. The frequency domain representation may include only one or more selected frequency bands, which may correspond to one or more frequencies commonly found in speech.

Power calculator 316 may receive the frequency domain representations and determine one or more power parameters for each microphone 106, 108, 110. In general, each power parameter relates to the power of the microphone signal in the frequency domain. In particular, the power parameters may include only one or more selected frequency bands, which may correspond to one or more frequencies commonly found in speech.

In general, the power parameter calculation may be calculated according to the following equation:

$$\text{Power Parameter} = \sum_{k=f_i}^{f_i+N} W(A_k), \qquad (1)$$

where A is the amplitude of the signal in selected frequency band $f_i$, N is the total number of selected frequency bands, i is the index of the frequency bin, and $W(A_k)$ is a function of the magnitude. The power parameter is a function of the magnitude of the signal in the selected frequency bands.

Any suitable function W may be used to characterize the magnitude of the signal. For example, the power parameter may be calculated according to the following equation:

$$\text{Power Parameter} = \sum_{k=f_i}^{f_i+N} \frac{A_k^2}{N}, \qquad (2)$$

where A is the amplitude of the signal in selected frequency band $f_i$, N is the total number of selected frequency bands, and i is the index of the frequency bin. In this example, the magnitude of the signal is represented by a sum of the square of the amplitude of the signal in each selected frequency band divided by the total number of frequency bands.

As described herein, the one or more selected frequency bands may correspond to those found in typical human speech. In particular, the one or more selected frequency bands may include frequencies from about 100, 200, or even 300 Hz up to about 1200, 1100, or even 1000 Hz. In one example, the one or more selected frequency bands may range from about 300 up to 1000 Hz.

Ratio calculator 318 may receive the power parameters corresponding to each microphone 106, 108, 110 and provide a value that compares the power parameters. In some embodiments, a ratio is calculated between two or more power parameters. For example, a power parameter corresponding to one ambient microphone 108, 110 may be compared to the power parameter corresponding to voice microphone 106, for example, by using division to calculate the ratio therebetween. In another example, the power parameters corresponding to ambient microphones 108, 110 may be combined (e.g., averaged) and then compared to the power parameter corresponding to voice microphone 106, for example, by using division to calculate the ratio therebetween (e.g., a power ratio).

Comparator 320 may receive and compare the power ratio, or other comparative value from ratio calculator 318, to a threshold value. In particular, the comparator 320 may use a threshold ratio (e.g., threshold power ratio).

Voice decider 322 may make a determination based at least in part on the power parameters and a threshold value. In particular, voice decider 322 may determine whether a voice has been detected or not detected based on whether the power ratio exceeds the threshold power ratio. The voice power parameter corresponding to the voice microphone 106 may be used in the numerator of the ratio, and the ambient power parameter corresponding to at least one ambient microphone 108, 110 may be used in the denominator of the ratio. In general, when the voice power parameter corresponding to voice microphone 106 exceeds the power parameter corresponding to one or both ambient microphones 108, 110 by a certain amount, a voice is detected. In other words, voice decider 322 may determine that a voice is detected when the ratio of the power parameters (e.g., power ratio) exceeds the threshold ratio (e.g., threshold power ratio).

When a voice is detected, voice decider 322 may enable encoding and/or transmission of an audio signal based on the signal from voice microphone 106. When a voice is not detected, voice decider 322 may disable encoding and/or transmission.

Processor 306 may include audio enhancer 324, which may receive an audio signal and provide an enhanced audio signal. In particular, audio enhancer 324 may enhance the microphone signal of voice microphone 106. In some embodiments, audio enhancer 324 uses a noise reduction algorithm to provide the enhanced audio signal. In general, audio enhancer 324 uses the voice signal and at least one ambient signal. For example, audio enhancer 324 may use spectral subtraction to subtract magnitudes in one or more selected frequency bands of the ambient signal from the voice signal in the frequency domain. In another example, audio enhancer 324 may use a minimum mean square error (MMSE) algorithm using the voice signal and at least one ambient signal as inputs. The MMSE algorithm may provide fewer artifacts than spectral subtraction.

The MMSE algorithm may be used with the frequency domain representations of the voice signal and at least one ambient signal because, for example, when assuming that the spectral components of the speech and noise have gaussian distribution and are statistically independent. The estimated amplitude of the speech may be provided by the following equation:

$$\widehat{A_k} = \Gamma(1.5)\frac{\sqrt{v_k}}{\gamma_k}e^{\left(\frac{-v_k}{2}\right)}\left[(1+v_k)I_0\left(\frac{v_k}{2}\right)+v_k I_1\left(\frac{v_k}{2}\right)\right]R_k,$$

where $$\Gamma(1.5) = \frac{\sqrt{\pi}}{2};$$

where $I_0$ and $I_1$ denote the modified Bessel's function of zero and first order; where $v_k$ is defined by $$v_k \triangleq \frac{\xi_k}{1+\xi_k}\gamma_k,$$

where $$\xi_k \triangleq \frac{\lambda_x(k)}{\lambda_d(k)} \text{ and } \gamma_k \triangleq \frac{R_k^2}{\lambda_d(k)},$$

where $\lambda_x(k)$ and $\lambda_d(k)$ are the variances of the speech and noise spectral components respectively; where $R_k$ is the magnitude of the noisy (speech plus noise) spectral component; and where k is the index of the spectral component.

Processor 306 may include communications encoder 326, which may receive an audio signal (e.g., enhanced audio signal) and encode the audio signal to be transmitted (e.g., by transceiver 212). Any suitable encoding technique may be used, such as frequency modulation (FM), amplitude modulation (AM), ITU-T G.726, ITU-T G.727, or ITU-T G.729 encoding.

Processor 306 may be operably coupled to memory 308, which may be used to store data related to the execution of the one or more modules of the processor. Examples of data storable in memory 308 are schematically illustrated in FIG. 4.

Figure 4:
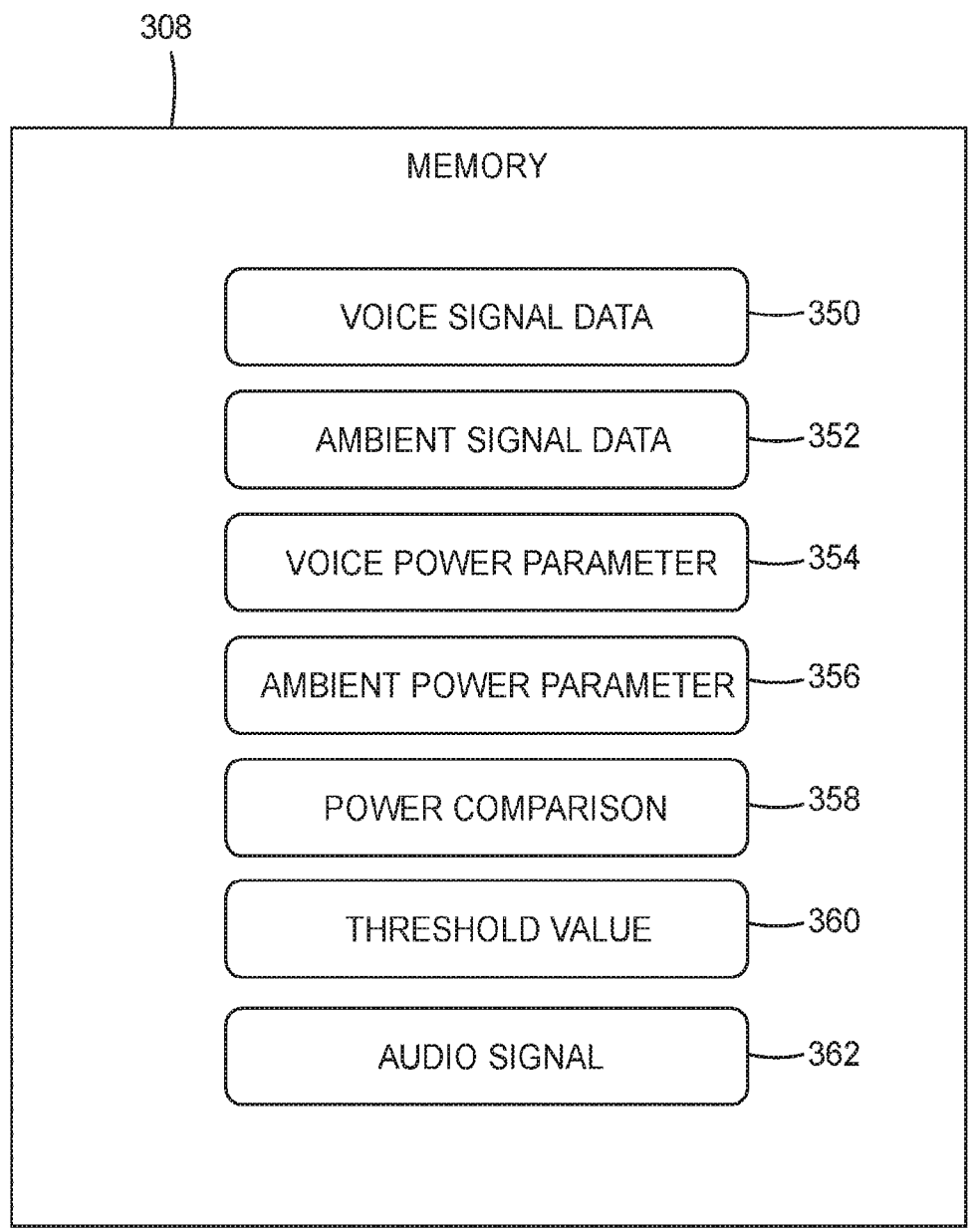
FIG. 4 is a schematic illustration of a memory storing data in the controller of FIG. 3 according to one embodiment of the present application.

In FIG. 4, memory 308 may be used to store voice signal data 350 representing the voice signal in digital form. Memory 308 may be used to store ambient signal data 352 representing to one or more ambient signals in digital form. Voice power parameter 354 and ambient power parameter 356 calculated by processor 306 may be stored in memory 308. Power comparison 358 may be stored in memory 308, for example, as a power ratio. Memory 308 may store threshold value 360, which may be retrieved, for example, to compare with the power ratio. Threshold value 360 may include a one threshold value or different threshold values. In some embodiments, the threshold values for enabling and disabling encoding and/or transmission are the same or equal. In other embodiments, the threshold values for enabling and disabling encoding and/or transmission are different. Each threshold value 360 may be tuned for the particular hardware of the headset being used. Each threshold value 360 may be determined using trial and error for the particular hardware. Audio signal 362, which may be enhanced, may be stored in memory 308 before being transmitted.

With various components of headset 102 (FIG. 1) being described, various methods relate to voice-activated encoding are described herein that may be used with the headset with reference to FIGS. 5 to 8.

Figure 5:
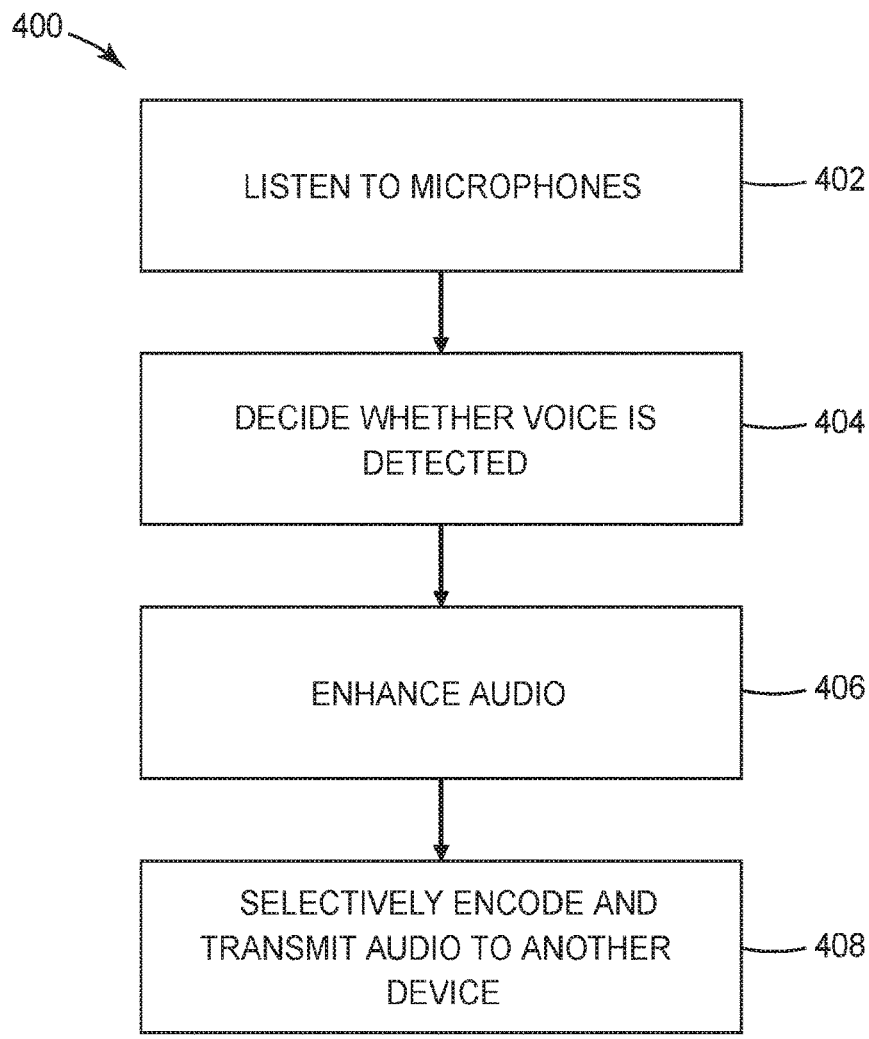
FIG. 5 is a flow diagram of another method of voice-activated encoding for use with the headset of FIG. 1 according to one embodiment of the present application.

In FIG. 5, one method 400 for voice-activated encoding is illustrated, which may be carried out using various components of headset 102. Method 400 may include listening to microphones 402. Based on signals from the microphones, method 400 may decide whether a voice is detected 404. If a voice is detected, method 400 may enhance the audio 406 before transmission. Method 400 may selectively encode and/or transmit audio to another device 408 if a voice is detected. The audio may or may not be enhanced. If a voice is not detected, method 400 may disable encoding and/or transmission of audio.

Figure 6:
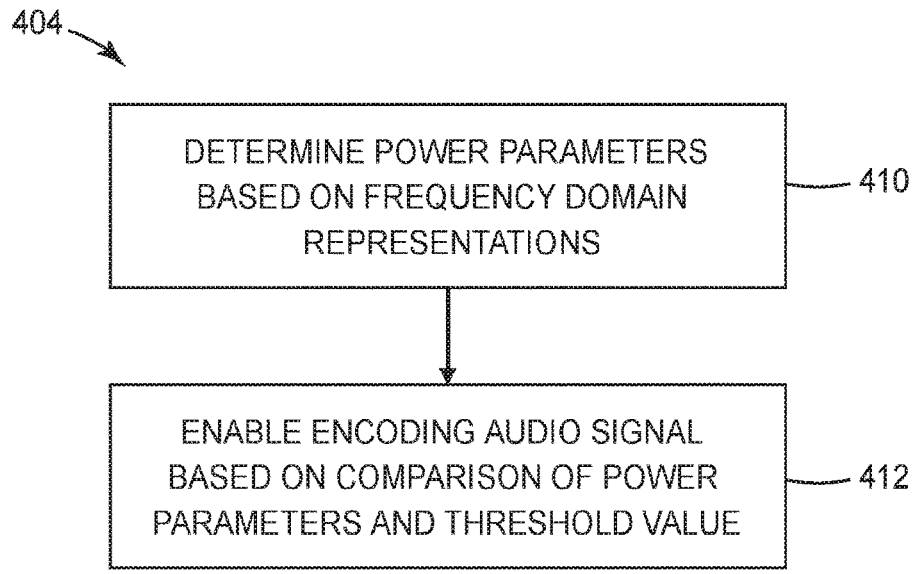
FIG. 6 is a flow diagram of one method of deciding whether a voice is detected for use with the method of FIG. 5 according to one embodiment of the present application.

In FIG. 6, one example of method 404 of deciding whether a voice is detected is illustrated. Method 404 may include determining power parameters based on frequency domain representations of microphone signals 410. At least two microphone signals may be used, for example, one for a voice signal and one for an ambient signal. Method 404 may include enabling encoding of an audio signal based on the comparison of the power parameters and a threshold value. For example, the comparison of the power parameters may produce a value (e.g., a ratio), which then may be compared to the threshold value (e.g., a threshold ratio).

Figure 7:
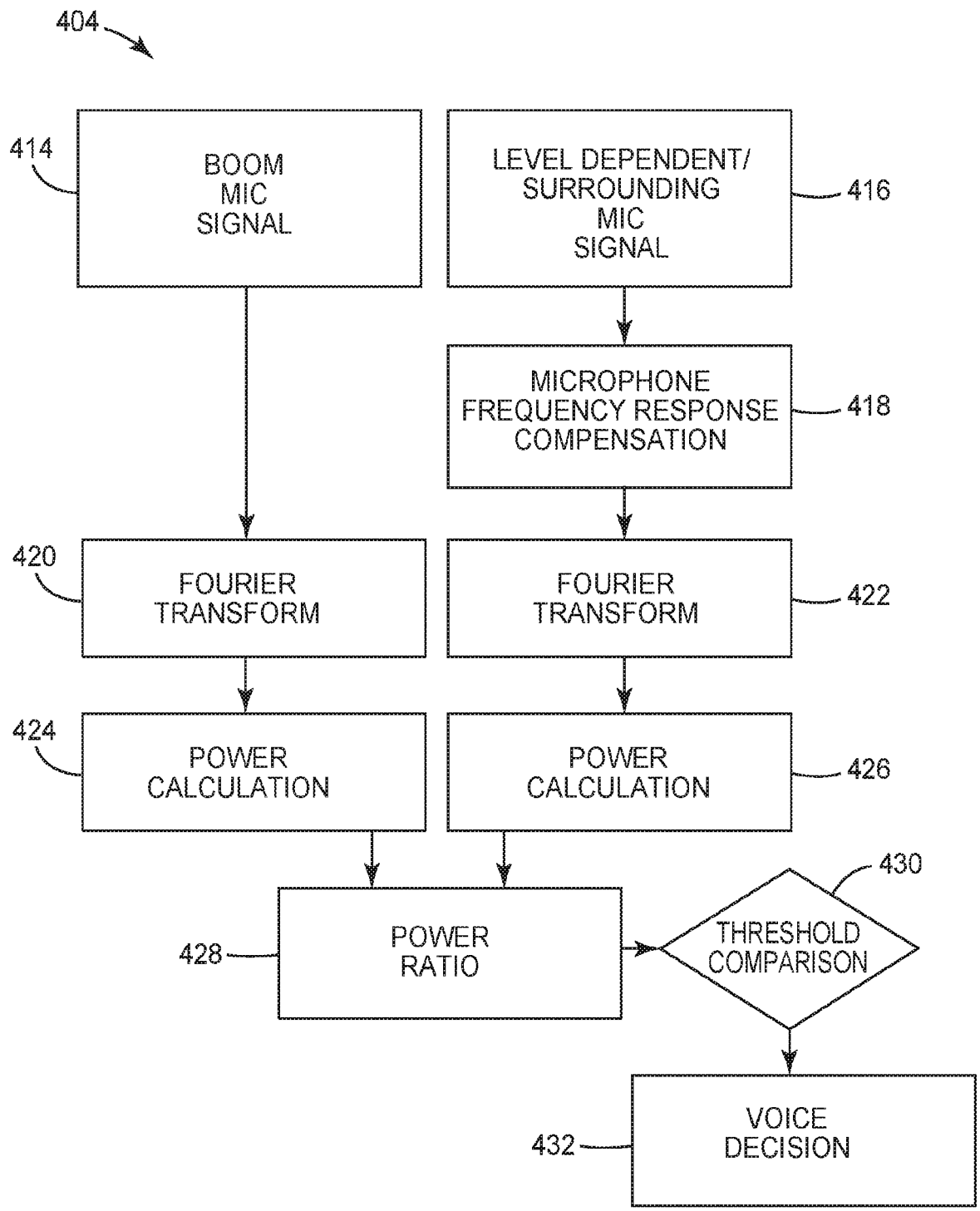
FIG. 7 is a flow diagram of another method of deciding whether a voice is detected for use with the method of FIG. 5 according to one embodiment of the present application.

In FIG. 7, another example of method 404 of deciding whether a voice is detected is illustrated in more detail than FIG. 6. Method 404 may include receiving a voice signal from a voice microphone on a boom 414 and may include receiving at least one ambient signal from one or more ambient microphones 416. The ambient microphones may be positioned to receive surrounding sound other than the voice of the user. As illustrated, one or more of the ambient signals may be compensated based on frequency response 418. Using frequency compensation may provide a more accurate comparison of the voice signal with the ambient signals.

One or more microphones, such as ambient microphones 416, may be level dependent. As used herein, "level dependent" refers to adjusting the level of one or more microphones of a headset based on the level of the surrounding (e.g., ambient) sounds, which may help protect the hearing of the user. A level dependent function (LDF) may be used to calibrate the level of ambient microphones 416.

Method 404 may include applying a Fourier Transform (e.g., Fast Fourier Transform, or FFT) to the voice signal 420 and applying a Fourier Transform to one or more of the ambient signals 422 to provide frequency domain representations for the voice and ambient signals.

The frequency domain representations may be used in method 404 to provide a power parameter for the voice signal 424 and at least one power parameter for the ambient signal 426. The power parameters may be compared in method 404 by calculating a power ratio between at least two of the power parameters 428 (e.g., a ratio between the voice power parameter and an average of the ambient power parameters). In particular, the voice power parameter may correspond to the numerator of the power ratio and the ambient power parameters may correspond to the denominator of the power ratio. A higher voice power parameter may indicate a louder voice and may result in a higher power ratio.

Method 404 may include comparing the power ratio to a threshold power ratio 430, for example, to see whether the power ratio exceeds the threshold power ratio. Method 404 may include deciding whether a voice is detected 432 based on the comparison of the power ratio to the threshold power ratio. When the power ratio exceeds the threshold power ratio, a voice is detected.

Figure 8:
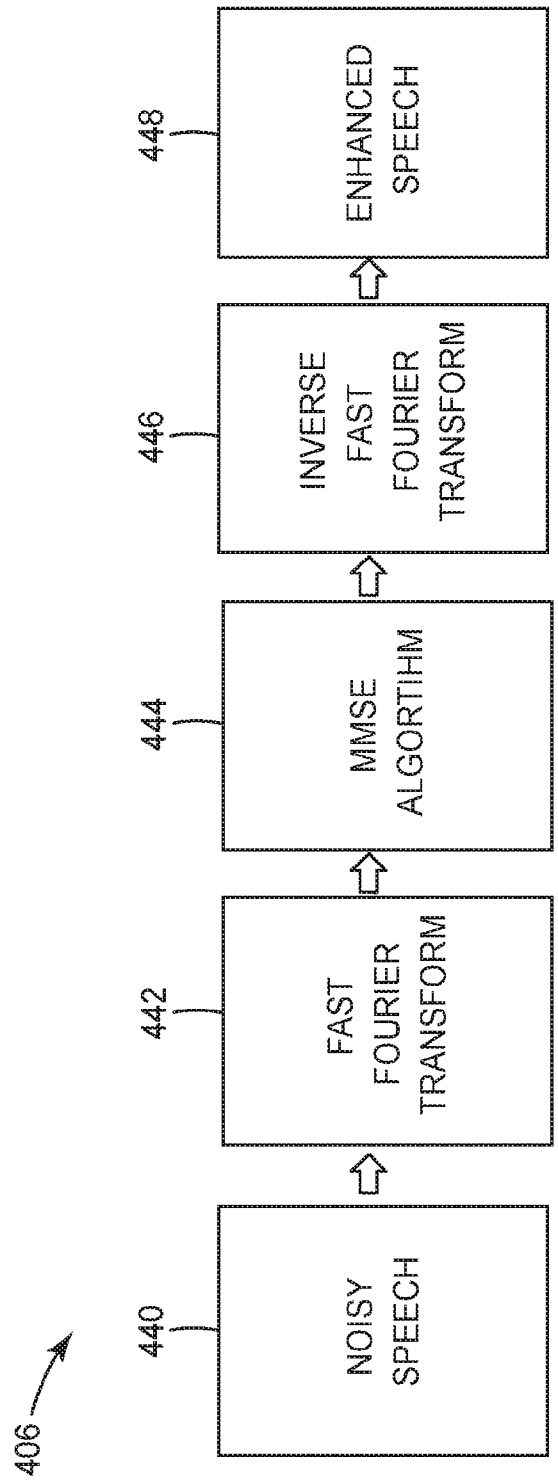
FIG. 8 is a flow diagram of one method of enhancing audio for use with the method of FIG. 5 according to one embodiment of the present application.

In FIG. 8, one example of method 406 of enhancing audio is illustrated. Method 406 may include receiving noisy speech 440. One or more signals representing the noisy speech may be transformed into a frequency domain representation 442, for example, using an FFT. The frequency domain representations may be used as inputs into a noise reduction algorithm 444 (e.g., an MMSE algorithm). The output of the noise reduction algorithm may be transformed into a time domain representation 446, for example, using an inverse FFT. The time domain representation may be used to provide an enhanced audio or speech 448, which may be encoded and/or transmitted to another device.

With various examples and illustrative embodiments of voice-activated sound encoding for headsets being described, various examples are described herein to further illustrate various technical effects and benefits and various combinations that may be used.

EXAMPLES

A communications headset incorporating ambient and voice microphones as shown in FIG. 1 was used in the following examples. The headset was placed on a BRÜEL & KJÆR (Nærum, Denmark) Type 4128C head and torso simulator (HATS) in a closed acoustic room with loudspeakers. The HATS also had a mouth simulator which was used to provide a voice signal to the boom microphone. The loudspeakers were used to introduce the noise signals into the environment. Prerecorded signals representative of voice, helicopter noise or pink noise were used to simulate voice-activated encoding performance for speech and speech in noisy environments, which may include helicopter noise or pink noise. The noise signals were produced at 85 and 105 dBA SPL and recorded along with the voice signal using a soundcard connected to a personal computer. All signals were recorded at a 32 kHz sample rate with 16-bit sample resolution. The digitized recordings were post-processed on the personal computer using Adobe Audition (San Jose, Calif.) software to synchronize the timing.

Table 1 describes the parameters and equations used in the prior art VOX algorithm A and in the exemplary VOX algorithm B of the present disclosure, wherein MB is the magnitude of the boom mic signal and MC is the magnitude of the compensated surround mic signal.

TABLE 1

| VOX OPERATIONAL PARAMETERS | | |
| --- | --- | --- |
| PARAMETER | VOX A | VOX B |
| Sampling Frequency | 32 kHz | 32 kHz |
| Frame length | 10 ms | 10 ms |
| Power Parameter(s) | $\sum_{k=f_i}^{F_i+N} \frac{MB_k^2}{N}$ | $\sum_{k=f_i}^{f_i+N} \frac{MB_k^2}{N}$ $\sum_{k=f_i}^{f_i+N} \frac{MC_k^2}{N}$ |
| Power Threshold | 3 | 3 |
| FFT Length | 512 | 512 |
| FFT Window | 'Hanning' | 'Hanning' |
| Lower Frequency Bin | 200 Hz | 200 Hz |
| Higher Frequency Bin | 1000 Hz | 1000 Hz |
| Decision Delay Time | 10 ms | 10 ms |
| Decision Hold Over Time | 500 ms | 500 ms |

Figure 9:
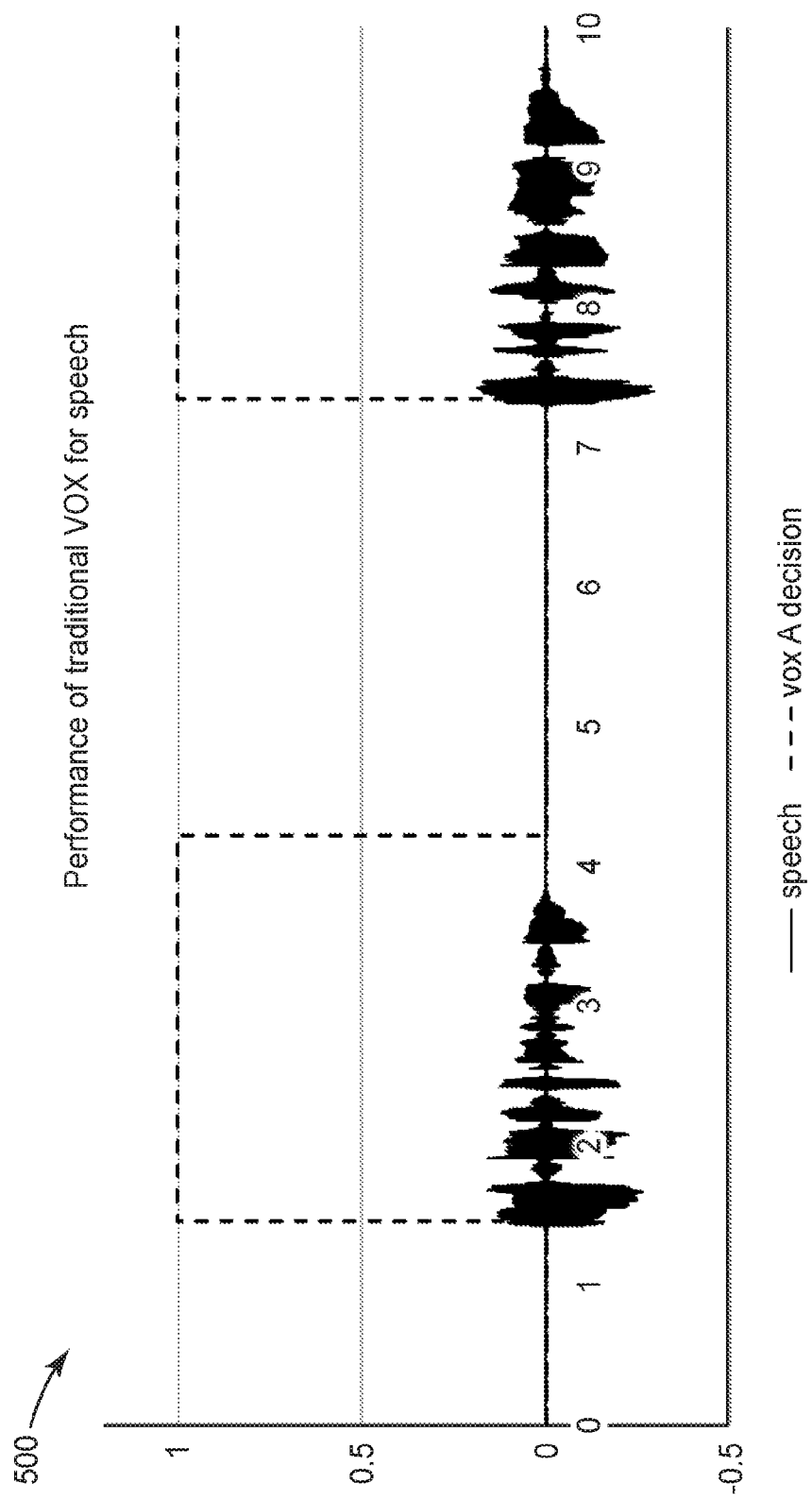
FIG. 9 is a plot showing VOX algorithm performance for a speech signal input.

In Example 1, the speech signal was used as an input to VOX algorithm A (e.g., a traditional VOX) to show one example of expected performance of the VOX algorithms before noise was introduced. Results are shown in plot 500 of FIG. 9, showing a representation of the speech signal amplitude and the VOX algorithm decisions over a time period of about 10 seconds. The sample data along the x-axis (e.g., time) was normalized to a range from 0 to 10. The VOX algorithm was limited to binary values: 0 for no speech detected and 1 for speech detected. As can be seen in FIG. 9, the VOX algorithm first began to detect the speech signal at about 1.5 and stopped at about 4.2 and second began to detect speech at about 7.4 and stopped sometime after 10.

Figure 10:
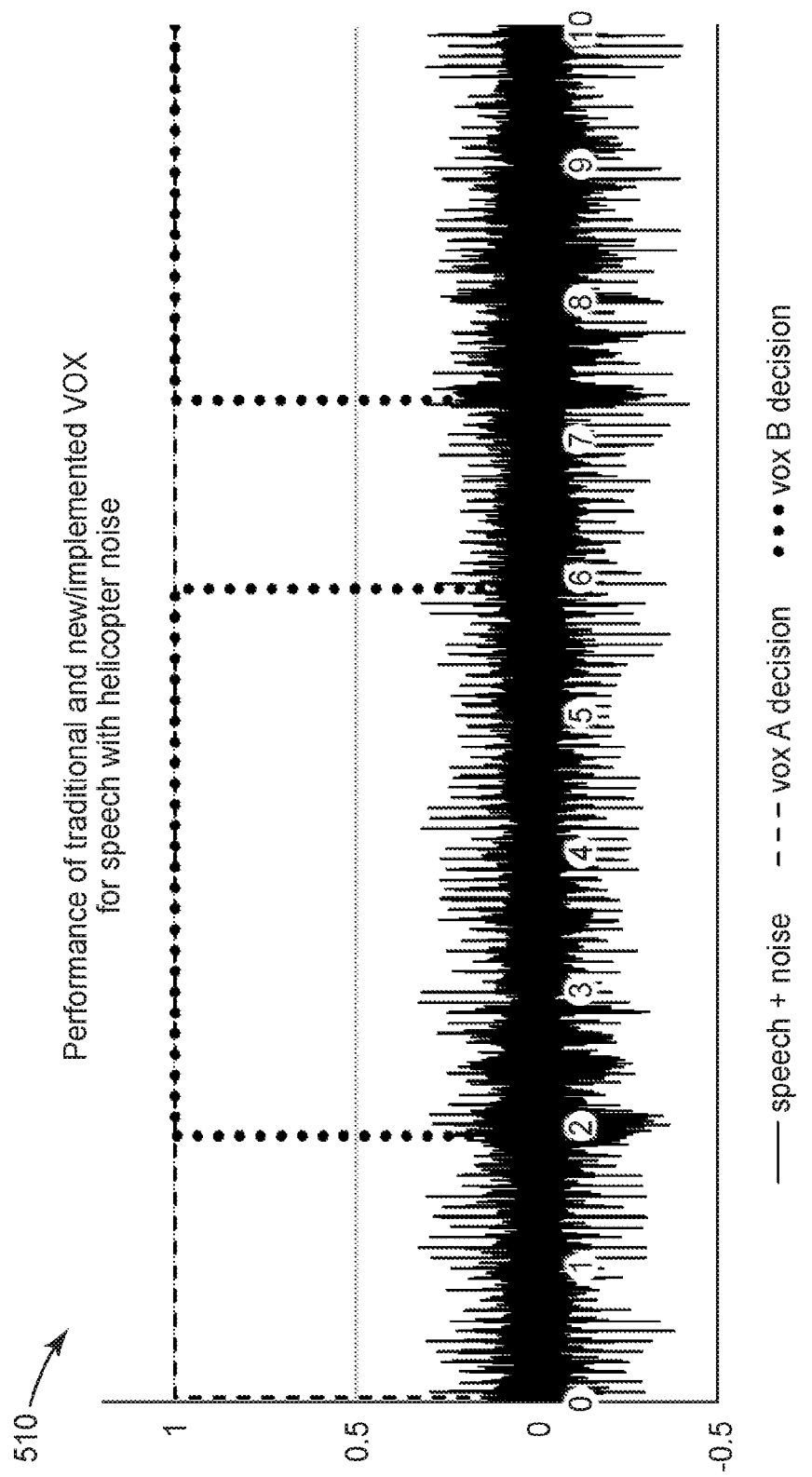
FIG. 10 is a plot showing performance of two VOX algorithms for a speech plus helicopter noise signal.

In Example 2, the speech signal was combined with the helicopter noise signal and used as an input to VOX algorithm A (e.g., a traditional VOX) and VOX algorithm B (e.g., a new/implemented VOX). Results are shown in plot 510 of FIG. 10, showing a representation of the speech plus helicopter noise signal and the decisions of the VOX algorithms A and B over a time period of about 10 seconds. The sample data along the x-axis (e.g., time) was normalized to a range from 0 to 10. The VOX algorithms were limited to binary values: 0 for no speech detected and 1 for speech detected. As can be seen in FIG. 10, VOX algorithm A began to detect the speech plus helicopter noise signal just after time 0 and stopped sometime after 10, indicating an inability of VOX algorithm A to recognize speech in the combined signal. On the other hand, VOX algorithm B first began to detect the speech signal in the combined speech plus helicopter noise signal at about 1.9 and stopped at about 5.9 and second began to detect speech at about 7.3 and stopped sometime after 10. The improvement in performance is believed to be due to the use of the additional information from the ambient microphone.

Figure 11:
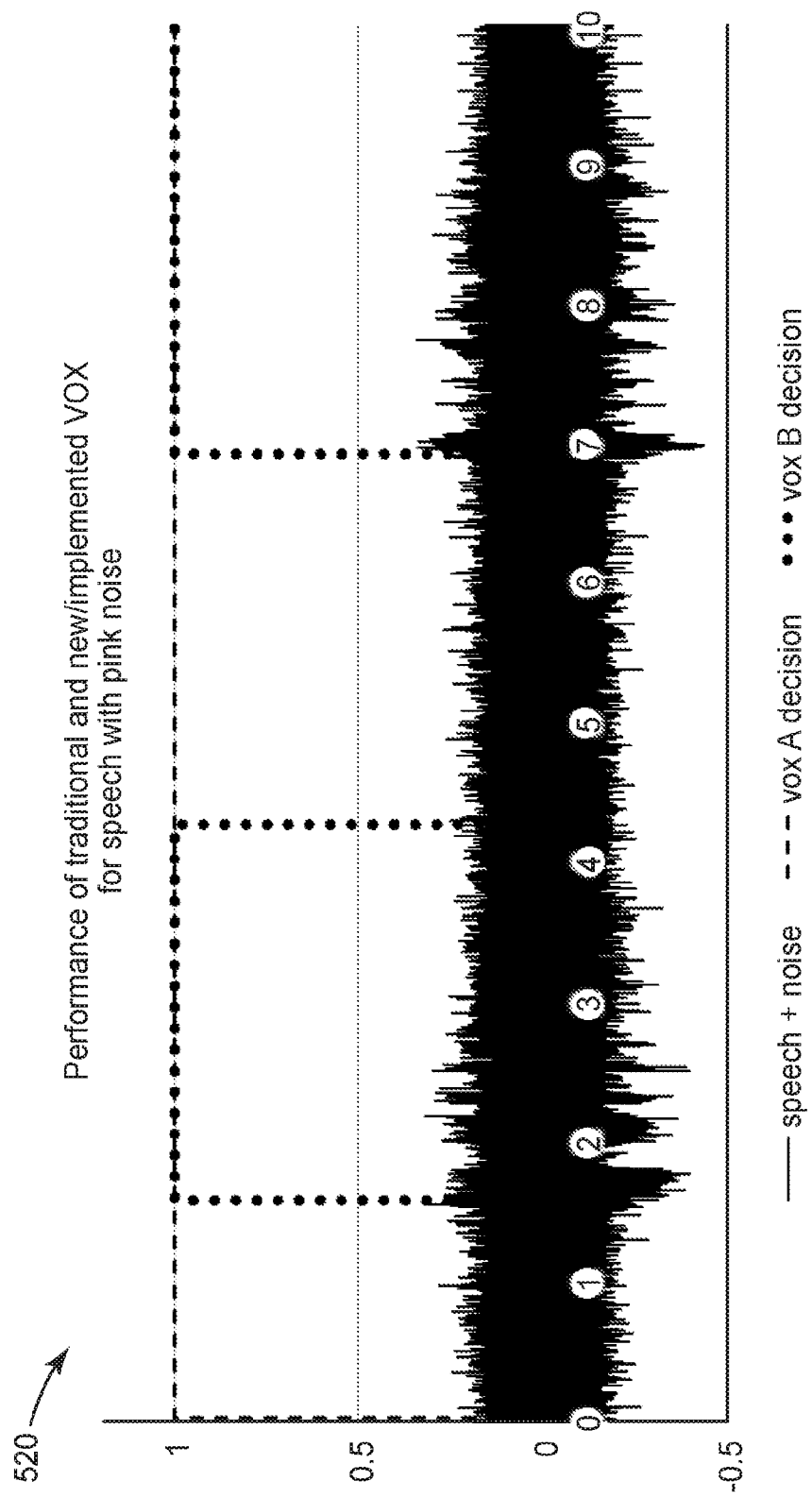
FIG. 11 is a plot showing performance of two VOX algorithms for a speech plus pink noise signal.

In Example 3, the speech signal was combined with the pink noise signal and used as an input to VOX algorithm A (e.g., a traditional VOX) and VOX algorithm B (e.g., a new/implemented VOX). Results are shown in plot 520 of FIG. 11, showing a representation of the speech plus pink noise signal and the decisions of the VOX algorithms A and B over a time period of about 10 seconds. The sample data along the x-axis (e.g., time) was normalized to a range from 0 to 10. The VOX algorithms were limited to binary values: 0 for no speech detected and 1 for speech detected. As can be seen in FIG. 11, VOX algorithm A began to detect speech just after time 0 and stopped sometime after 10, indicating an inability of VOX algorithm A to recognize speech in the combined signal. On the other hand, VOX algorithm B first began to detect speech in the combined speech plus pink noise signal at about 1.6 and stopped at about 4.2 and second began to detect speech at about 6.9 and stopped sometime after 10. The improvement in performance is believed to be due to the use of the additional information from the ambient microphone.

Illustrative Embodiments

In various illustrative embodiments, a device may include a voice microphone configured to generate a voice signal based on sound detected at the voice microphone. The device may also include at least one ambient microphone spaced from the voice microphone and configured to generate at least one ambient signal based on sound detected at the at least one ambient microphone. The device may further include a controller operably coupled to the microphones. The controller may include a communications encoder configured to encode an audio signal for transmission to another device. The controller may be configured to determine a voice power parameter based on a frequency domain representation of the voice signal. The controller may also be configured to determine an ambient power parameter based on a frequency domain representation of the at least one ambient signal. The controller may further be configured to, in response to a determination that is based at least in part on the power parameters and a threshold value, encode, using the communications encoder, an audio signal based on the voice signal.

In various illustrative embodiments, a controller may include an input interface configured to receive a voice signal and at least one ambient signal. The controller may also include an output interface configured to provide an audio signal based on the voice signal. The controller may further include a memory configured to store a representation of the voice signal and the ambient signal. In addition, the controller may include a processor operably coupled to the input interface, the output interface, and the memory. The processor may be configured to determine a voice power parameter based on a frequency domain representation of the voice signal. The processor may also be configured to determine an ambient power parameter based on a frequency domain representation of the at least one ambient signal. The processor may further be configured to, in response to a determination that is based at least in part on the power parameters and a threshold value, encode an audio signal based on the voice signal.

In various illustrative embodiments, a method may include determining a voice power parameter based on a frequency domain representation of a voice signal from a voice microphone. The method may also include determining an ambient power parameter based on a frequency domain representation of at least one ambient signal from at least one ambient microphone spaced from the voice microphone. The method may further include encoding, using a microprocessor, an audio signal based on the voice signal in response to a determination that is based at least in part on the power parameters and a threshold value.

In one or more illustrative embodiments, encoding may be disabled based on the comparison of the power parameters and a threshold value, which may be the same or different than the threshold value for enabling encoding.

In one or more illustrative embodiments, transmission may be enabled or disabled based on whether encoding is enabled or disabled, respectively.

In one or more illustrative embodiments, a ratio may be determined between the power parameters. The power parameters may be compared using a ratio between the power parameters.

In one or more illustrative embodiments, the ratio between the power parameters may be compared to a threshold ratio as the threshold value.

In one or more illustrative embodiments, the corresponding frequency domain representations may be determined using at least one of a Discrete Fourier Transform, a filter bank, or a wavelet transform.

In one or more illustrative embodiments, corresponding power parameters may be determined based on magnitudes in selected frequency bands.

In one or more illustrative embodiments, the voice signal and the at least one ambient signal may be converted from analog to digital before determining the corresponding power parameters.

In one or more illustrative embodiments, the at least one ambient signal may be compensated based on differences in frequency response of the at least one ambient microphone and the voice microphone.

In one or more illustrative embodiments, an enhanced audio signal may be provided as the audio signal based on the frequency domain representation of the voice signal and the frequency domain representation of the at least one ambient signal using a noise reduction algorithm.

In one or more illustrative embodiments, a magnitude of the audio signal may be determined based on the voice signal and the at least one ambient signal using a noise reduction algorithm. The audio signal may be provided based on the determined magnitude.

In one or more illustrative embodiments, the at least one ambient microphone may include first and second ambient microphones spaced from the voice microphone.

In one or more illustrative embodiments, a first earpiece and a second earpiece may be included. Each earpiece may have a speaker and a respective one of the first and second ambient microphones.

In one or more illustrative embodiments, a headband extending between the first and second earpieces may be included.

In one or more illustrative embodiments, a boom extending from one of the first and second earpieces to the voice microphone may be included.

In one or more illustrative embodiments, a transceiver configured to transmit the encoded audio signal may be included.

Thus, various aspects, examples, and embodiments of Voice-Activated Sound Encoding for Headsets Using Frequency Domain Representations of Microphone Signals are disclosed. Although reference is made herein to the accompanying set of drawings that form part of the present application, one of at least ordinary skill in the art will appreciate that various adaptations and modifications of the embodiments described herein are within, or do not depart from, the scope of the disclosure of the present application. For example, aspects of the embodiments described herein may be combined in a variety of ways with each other. Therefore, it is to be understood that, within the scope of the appended claims, the claimed invention may be practiced other than as explicitly described herein.

In particular, it will be understood that each block of the block diagrams and combinations of those blocks can be implemented by means for performing the illustrated function.

All references and publications cited herein are expressly incorporated herein by reference in their entirety into the disclose of the present application, except to the extent they may directly contradict this disclosure.

All scientific and technical terms used herein have meanings commonly used in the art unless otherwise specified. The definitions provided herein are to facilitate understanding of certain terms used frequently herein and are not meant to limit the scope of the disclosure of the present application.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a controller operably coupled to a transceiver may allow the controller to transmit signals using the transceiver).

The term "and/or" means one or all of the listed elements or a combination of at least two of the listed elements (e.g., a microphone and/or a speaker means a microphone, a speaker, or both the microphone and the speaker).

What is claimed is:

1. A device comprising:
    a voice microphone configured to generate a voice signal based on sound detected at the voice microphone;
    at least one ambient microphone spaced from the voice microphone and configured to generate at least one ambient signal based on sound detected at the at least one ambient microphone; and
    a controller operably coupled to the microphones, the controller comprising a communications encoder configured to encode an audio signal for transmission to another device, the controller configured to:
    determine a voice power parameter based on a frequency domain representation of the voice signal;
    determine an ambient power parameter based on a frequency domain representation of the at least one ambient signal;
    determine a ratio of the voice power parameter and the ambient power parameter, compare the ratio to a threshold value and based on the comparison, detect a voice; and
    in response to a detected voice, encode, using the communications encoder, an audio signal and if the comparison indicates a voice is not detected, not encoding the audio signal.

2. The device of claim 1, wherein if based on the comparison, a voice is not detected, disabling communication encoder.

3. The device of claim 1, wherein the controller is configured to determine the corresponding frequency domain representations using at least one of a Discrete Fourier Transform, a filter bank, or a wavelet transform.

4. The device of claim 1, wherein the controller is configured to determine the corresponding power parameters based on magnitudes in selected frequency bands.

5. The device of claim 1, wherein the controller is configured to convert the voice signal and the at least one ambient signal from analog to digital before determining the corresponding power parameters.

6. The device of claim 1, wherein the controller is configured to compensate the at least one ambient signal based on differences in frequency response of the at least one ambient microphone and the voice microphone.

7. The device of claim 1, wherein the controller is configured to provide an enhanced audio signal as the audio signal based on the frequency domain representation of the voice signal and the frequency domain representation of the at least one ambient signal using a noise reduction algorithm.

8. The device of claim 1, wherein the at least one ambient microphone comprises first and second ambient microphones spaced from the voice microphone.

9. The device of claim 8, further comprising a first earpiece and a second earpiece, each earpiece comprising a speaker and a respective one of the first and second ambient microphones.

10. The device of claim 9, further comprising:
a headband extending between the first and second earpieces; and
a boom extending from one of the first and second earpieces to the voice microphone.

11. A controller comprising:
an input interface configured to receive a first signal and a second signal, wherein the second signal is an ambient signal;
an output interface configured to provide an audio signal is a voice is detected;
a memory configured to store a representation of the first and second signals; and
a processor operably coupled to the input interface, the output interface, and the memory, the processor configured to:
determine a first power parameter based on a frequency domain representation of the first signal;
determine a second power parameter based on a frequency domain representation of the signal;
generate a ratio of the first power parameter to the second power parameter and, if the ratio exceeds a threshold, detect a voice:
in response to the voice detection, encode the audio signal and if the comparison indicates a voice is not detected, not encoding the audio signal.

12. The controller of claim 11, wherein the audio signal is encoded based on the first or second signal.

13. The controller of claim 11, wherein the processor is configured to determine the corresponding frequency domain representations using at least one of a Discrete Fourier Transform, a filter bank, or a wavelet transform.

14. The controller of claim 11, further comprising:
a transceiver configured to transmit the encoded audio signal.

15. The controller of claim 11, wherein the processor is configured to convert the voice signal and the at least one ambient signal from analog to digital before determining the corresponding power parameters.

16. The controller of claim 11, wherein the processor is configured to compensate the at least one ambient signal based on differences in frequency response of the at least one ambient microphone and the voice microphone.

17. The controller of claim 11, wherein the processor is configured to provide an enhanced audio signal as the audio signal based on the frequency domain representation of the voice signal and the frequency domain representation of the at least one ambient signal using a noise reduction algorithm.

18. A method comprising:
determining a voice power parameter based on a frequency domain representation of a voice signal from a voice microphone;
determining an ambient power parameter based on a frequency domain representation of at least one ambient signal from at least one ambient microphone spaced from the voice microphone;
generating a ratio between the voice power parameter and the ambient power parameter and comparing that ratio to the threshold;
if the comparison indicates a voice is detected, encoding, using a microprocessor, an audio signal based on the voice signal; and
if the comparison indicates a voice is not detected, not encoding an audio signal.

19. The method of claim 18, wherein generating the ratio comprises:
determining the corresponding power parameters based on magnitudes in selected frequency bands; and
comparing the power parameters using a ratio between the power parameters; and
comparing the ratio to a threshold ratio as the threshold value.

20. The method of claim 18, further comprising:
determining a magnitude of the audio signal based on the voice signal and the at least one ambient signal using a noise reduction algorithm; and
providing the audio signal based on the determined magnitude.

* * * * *

UNITED STATES PATENT AND TRADEMARK OFFICE
CERTIFICATE OF CORRECTION

PATENT NO. : 11,418,866 B2
APPLICATION NO. : 15/733658
DATED : August 16, 2022
INVENTOR(S) : Stefan Mikael Apelqvist Page 1 of 1

It is certified that error appears in the above-identified patent and that said Letters Patent is hereby corrected as shown below:

In the Claims

Column 17
Line 18, In Claim 11, delete "is a voice" and insert -- if a voice --, therefor.

Signed and Sealed this
Third Day of October, 2023

Katherine Kelly Vidal
*Director of the United States Patent and Trademark Office*